(12) United States Patent
Tsubota

(10) Patent No.: US 6,823,764 B1
(45) Date of Patent: Nov. 30, 2004

(54) APPARATUS FOR BORING STOMA WAFERS

(75) Inventor: Tatsuji Tsubota, Okayama (JP)

(73) Assignee: Tsubota Kosakusho Ltd., Okayama (JP)

( * ) Notice: Subject to any disclaimer, the term of this patent is extended or adjusted under 35 U.S.C. 154(b) by 0 days.

(21) Appl. No.: 09/451,629

(22) Filed: Nov. 30, 1999

(30) Foreign Application Priority Data

Dec. 1, 1998 (JP) .......................................... P10-342075

(51) Int. Cl.$^7$ ................................................ B26F 1/02
(52) U.S. Cl. .............................. 83/249; 83/36; 83/631; 83/684; 30/316; 30/360; 33/30.1
(58) Field of Search .......................... 30/300, 301, 310, 30/316, 130, 299, 288, 289, 293, 294, 315, 320, 358, 359, 360, 361, 362, 368; 83/36, 249, 621, 631, 684, 745; 33/27.01, 27.04, 30.1

(56) References Cited

U.S. PATENT DOCUMENTS

| | | | |
|---|---|---|---|
| 1,513,478 A | * 10/1924 | Bourque ...................... | 30/130 |
| 2,314,535 A | * 3/1943 | Worden ...................... | 33/27.04 |
| 3,091,855 A | * 6/1963 | Hart ............................. | 30/359 |
| 4,391,042 A | 7/1983 | Sunderland ................. | 30/316 |
| 4,817,287 A | 4/1989 | Arnold et al. .............. | 30/178 |
| 4,924,574 A | 5/1990 | Jones et al. ................. | 30/115 |
| 5,079,843 A | * 1/1992 | Shelton et al. .............. | 30/310 |
| 5,361,664 A | * 11/1994 | Desmarais ................... | 83/628 |
| 6,286,216 B1 | * 9/2001 | Braun ......................... | 30/310 |

* cited by examiner

Primary Examiner—Clark F. Dexter
(74) Attorney, Agent, or Firm—Koda & Androlia

(57) ABSTRACT

An apparatus for boring stoma wafers is provided, which comprises a base and a cutter, and enables even a user himself to easily make in a stoma wafer a substantially elliptic hole having a beautiful inner circumference. The base comprises an upper base member on which a stoma wafer is placed so that the stoma wafer can be temporarily fixed thereon, and a lower base member supporting the upper base member so that the upper base member can be moved freely. After a stoma wafer in which a circular hole has been made by the cutter is slid with the upper base member, a circular hole is bored again by the cutter in a position which is staggered from the center of the initially-formed circular hole, and this enables a non-circular hole comprising not less than two staggered circular holes to be made in the stoma wafer.

3 Claims, 14 Drawing Sheets

APPARATUS FOR BORING STOMA WAFERS

BACKGROUND OF THE INVENTION

1. Field of the Invention

This invention relates to an apparatus for making different holes suitable for different users in stoma wafers (including wafers for ureters and digestive tracts).

2. Description of the Prior Art

There are many people having their recta cut off due to various diseases and using stomata (artificial anuses). A stoma wafer has an external appearance seen in FIG. 6, a rear surface of which comprises an adhesive surface. A user or a nursing person bores a hole suitable for the user in the stoma wafer, and the resultant stoma wafer is pasted on the user's body for practical use. A pair of scissors capable of cutting a curvilinear opening have heretofore been used to make a hole in a stoma wafer. A conventional stoma wafer is provided in advance with a small hole (refer to FIG. 2) in the center thereof, into which a pair of scissors are inserted to cut off unnecessary portions of a hole-surrounding region so that a hole of a required size or shape is made.

A stoma wafer is mostly of the type which is provided with grooves concentric with a hole made therein in advance. When the stoma wafer is cut along any one of the grooves, a generally circular larger hole is obtained. However, different users require holes of different sizes or shapes, so that a hole to be newly obtained has to be formed to a substantially elliptic shape by cutting off the hole-surrounding portions of the stoma wafer. Since a margin to be additionally cut is as narrow as around 1–2 mm, the concentric grooves prevent a cutting operation from being carried out well, and a zigzag portion on which filth is deposited is necessarily formed on an inner edge of the resultant hole.

Some propositions have been made so as to solve these problems. For example, U.S. Pat. No. 4,817,287 discloses a stoma wafer boring apparatus comprising an annular cutting edge-carrying lever handle as a tool for making a circular hole accurately instead of scissors. U.S. Pat. No. 4,391,042 discloses a stoma wafer boring apparatus for forming a non-circular opening having a diagonal inner circumferential edge, and U.S. Pat. No. 4,924,574 discloses a stoma wafer boring apparatus provided with a gauge for regulating the position of an annular cutter in accordance with a diameter of a hole to be made.

However, it is still uneasy for a user himself to bore a non-circular (substantially elliptic) hole in a stoma wafer. Above all, it has been difficult to accurately measure a width of a margin to be cut which is as small as around 1–2 mm, and bore a desired non-circular hole in a stoma wafer. Under the circumstances, an apparatus for boring stoma wafers which enables a user himself to easily make a non-circular (substantially elliptic) hole having a beautiful inner edge has been discussed.

SUMMARY OF THE INVENTION

The present invention relates to an apparatus for boring stoma wafers comprising a base on which a stoma wafer is placed, a cutter for boring a circular hole in the stoma wafer placed on the base, and a guide rod for restricting a vertical movement of the cutter, the base comprising an upper base member on which the stoma wafer is placed so that the stoma wafer can be temporarily fixed thereon, and a lower base member supporting the upper base member so that the upper base member can be moved freely, the stoma wafer in which a circular hole has been bored by the cutter being slid laterally with the upper base member, the stoma wafer being then subjected in the slid position to a circular hole boring operation of the cutter again at the portion thereof which is staggered from the center of the initially formed circular hole, whereby a non-circular hole comprising not less than two staggered circular holes can be bored in the stoma wafer.

The present invention can be roughly divided into two types by the construction of the guide rod. A first type apparatus is formed by providing an elongated hole in an upper base member so that the hole extends in the moving direction of the upper base member, setting up a guide rod, which can be inserted through a hole provided in a stoma wafer, through the elongated hole from the lower base member, and providing a cutter so that the cutter moves down along the guide rod. To be exact, there are (1) a structure formed by fitting a cutter around a guide rod, and pressing down the cutter by a knob adapted to be moved down as the knob is screwed on the guide rod, (2) a structure having a cutter adapted to be moved down as the cutter is meshed with a guide rod, and (3) a structure formed by fitting a cutter around a guide rod, providing a spring, which is adapted to urge the cutter downward, between a cover put on the guide rod and the cutter, setting up a support base on a lower base member through an elongated hole of an upper base member, fixing a horizontally pivotable support handle to the support base, and providing the cutter with a circumferential groove adapted to enable the cutter to be lifted with a free end portion of the support handle inserted into the circumferential groove thereof, wherein the spring-urged cutter is pressed down by turning the support handle in the condition in which the support handle lifts the cutter with the free end portion of the former inserted into the circumferential groove of the latter to thereby make the free end portion escape from the groove.

The cutter is provided with a circular edge of a predetermined diameter extending around the guide rod. The stoma wafer is placed in a temporarily fixed state on the upper base member with the guide rod inserted therethrough, and the cutter is lowered along the guide rod to bore a circular hole concentric with the guide rod in the stoma wafer with the circular edge. The upper base member is then slid with the stoma wafer, and the cutter is lowered again to cut off an inner edge portion of the already-bored hole to form a substantially elliptic hole (non-circular hole comprising a combination of two staggered circular holes). The upper or lower base member is provided with a scale which permits an amount of relative movement of the two base members to be visually ascertained. In order to prevent the stoma wafer from being displaced, a clip for temporarily fixing the stoma wafer on the upper base member is provided thereon, or a recess for a separately formed clip, by which the stoma wafer is temporarily fixed to the upper base member, is provided in the upper base member. An upper base member movable in one direction meets the purpose satisfactorily in general. Accordingly, side edge guides extending in the direction of movement of the upper base member are provided on a lower base member so as to move the upper base member in one direction accurately.

In all of the above-described apparatuses for boring stoma wafers, a guide rod set up on a base is used as a vertical track, and accurate vertical movements of the cutter are attained. Other means capable of lowering the cutter accurately onto an upper base member may be used. Another apparatus for boring stoma wafers has also been developed which is formed by providing a lever and a rod-carrying cam via shafts on a frame set up on a lower base member so that the frame does not hinder a movement of the upper base member, and inserting through the frame a guide rod which operatively connects a cutter, which is provided between the upper base member and frame, and lever to each other to thereby form a means for urging the cutter upward, a circumferential edge portion of the cam turned by the rod turning down the lever to lower the guide rod with the cutter lowering toward the upper base member in accordance with this movement of the guide rod. Instead of providing the cutter with a means for urging the cutter upward, a means for urging the lever in the standing direction thereof may be provided on the lever.

In this apparatus for boring stoma wafers, the cutter can be lowered onto the upper base member accurately along the guide rod passed through the frame. This enables any projecting object to be eliminated from the upper surface of the base except a positioning projection of the stoma wafer. Therefore, the stoma wafer can be placed on the base easily, and the cutter and the circular edge thereof can be replaced easily. The guide rod is joined completely to the cutter but the direction in which the guide rod is moved up and down and the direction in which the lever is turned do not completely agree with each other. Therefore, regarding the lever, (1) a portion at which the guide rod and lever are joined to each other is set slidable in the longitudinal direction of the lever, or (2) an upper end of the guide rod is merely engaged with a lower surface of the lever. The urging means is provided on the cutter or lever with the function of moving back to an upper space the cutter which has just been subjected to a boring operation, and this means is formed by providing a spring between the frame and cutter or lever. When the urging means is provided on the cutter, the relation between the guide rod and lever may be either of (1) and (2) above. When the urging means is provided on the lever, the lever stands up to draw up the cutter via the guide rod, so that the relation (1) alone between the guide rod and lever can be adopted.

DESCRIPTION OF THE PREFERRED EMBODIMENTS:

The preferred modes of embodiment of the present invention will now be described.

Figure 1:
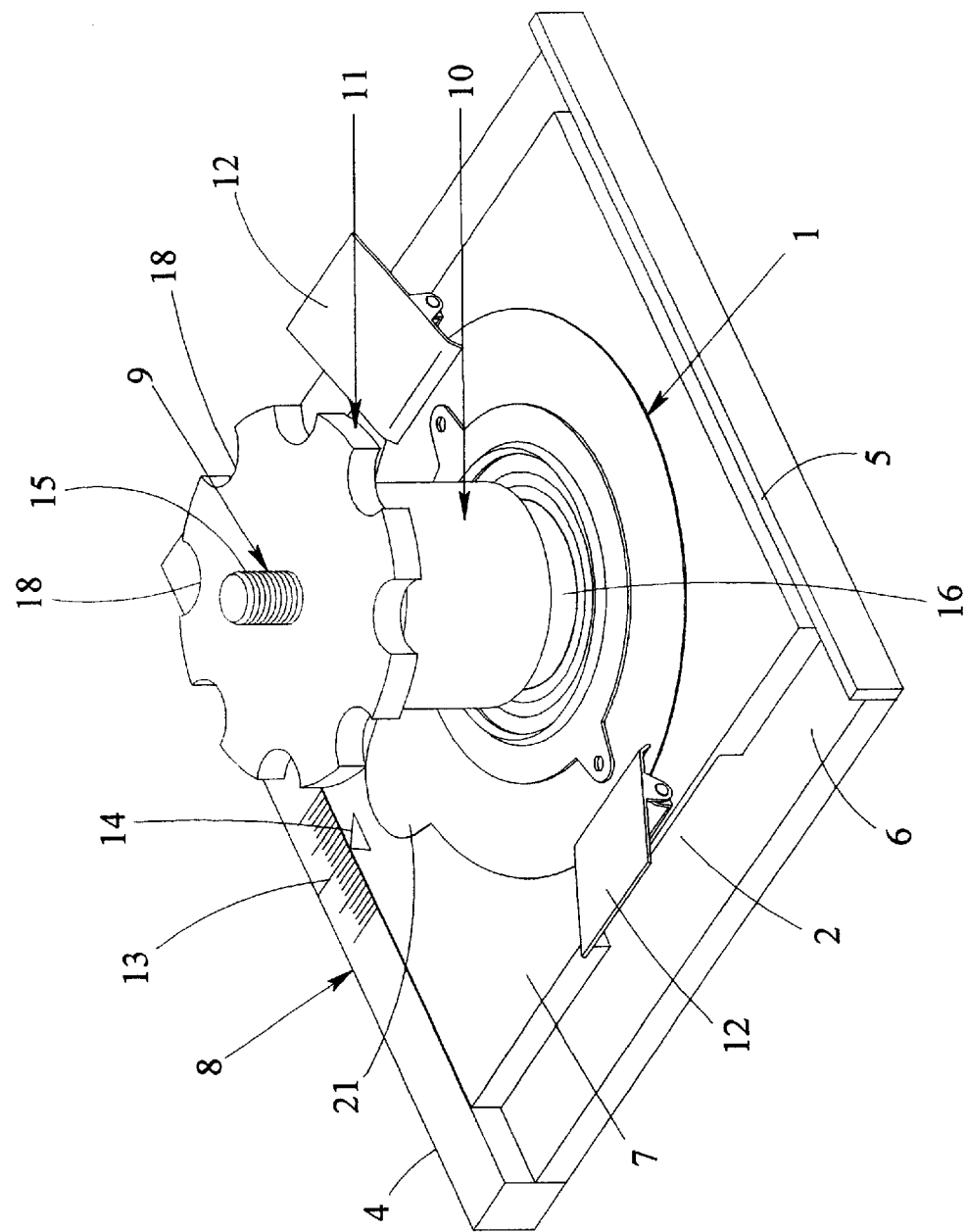
FIG. 1 is a perspective view showing the condition of a stoma wafer placed on a base and not yet bored in an example of the present invention.
Figure 2:
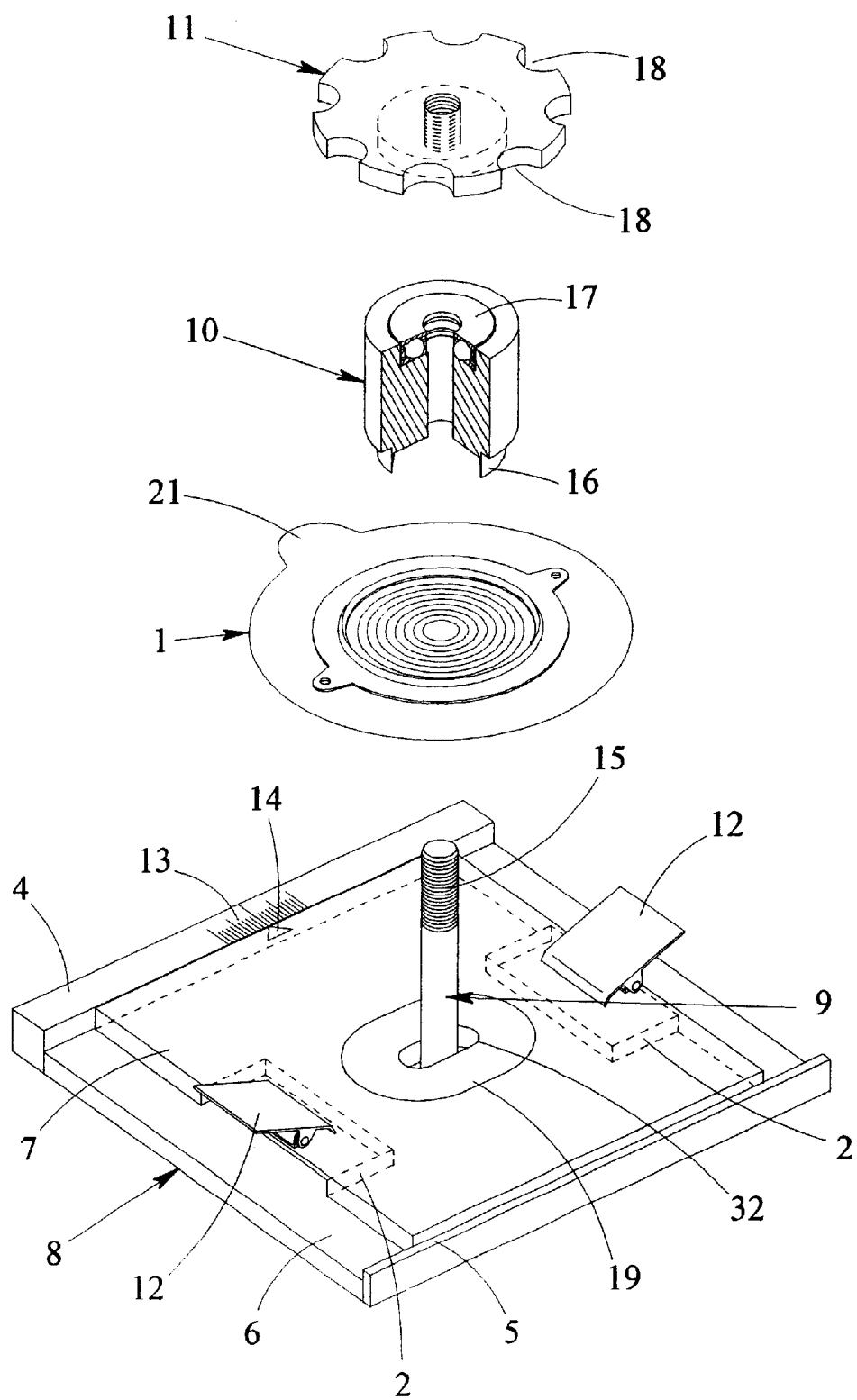
FIG. 2 is an exploded view in perspective showing the assembling relation between parts of the same example.

As seen in FIGS. 1 and 2, the apparatus for boring stoma wafers of this example comprises a base 8 in which an upper slidable base member 7 is placed on a lower base member 6 having side edge guides 4, 5 at both sides thereof, a guide rod 9 set up on the lower base member 6 through an elongated hole 32 provided substantially in the center of the upper base member 7 and extending in the sliding direction thereof, and a knob 11 screwed on a cutter 10, which is fitted around the guide rod 9. The upper base member 7 has thereon clips 12, 12 fixed thereto for positioning and setting the stoma wafer 1 placed thereon, and a reference mark 14 with respect to a scale 13 cut in one side portion of an edge guide 4. The stoma wafer 1 can be positioned and fixed in the recesses 2 by separately provided clips (not shown) instead of the clips 12 fixed to the upper base member 7. The guide rod 9 is provided with a male thread 15 on only the portion thereof on which the knob 11 is screwed, and the portion of the guide rod 9 around which the cutter 10 is fitted has a smooth surface.

In this example, the cutter 10 having a circular edge 16 at a lower. portion thereof is pressed by the knob 11 which is moved down as it is screwed on the guide rod 9. In order to prevent the cutter 10 from being turned by the turning. force of the knob, the cutter 10 is provided with a thrust bearing 17 on an upper surface thereof. The knob 11 is formed to a large diameter so that force is applied easily to the guide rod 9, and it is provided with regularly spaced recesses 18 for slip preventing purposes. The cutter 10 receives pressure from the knob 11 and cuts a circular hole in the stoma wafer 1. In order that the circular edge 16 cuts the stoma wafer 1 satisfactorily, the portion of the upper base member 7 which is opposed to the circular edge 16 has a receiving surface 19 of an ABS resin which the circular edge 16 bites. Instead of the ABS resin, other kinds of resins and rubber can also be utilized. When the circular edge 16 bites the receiving surface 19 too deep, the stoma wafer 1 is bitten together thereinto, and, therefore, an ABS resin softer than a metal and having a suitable hardness is optimally used.

Figure 3:
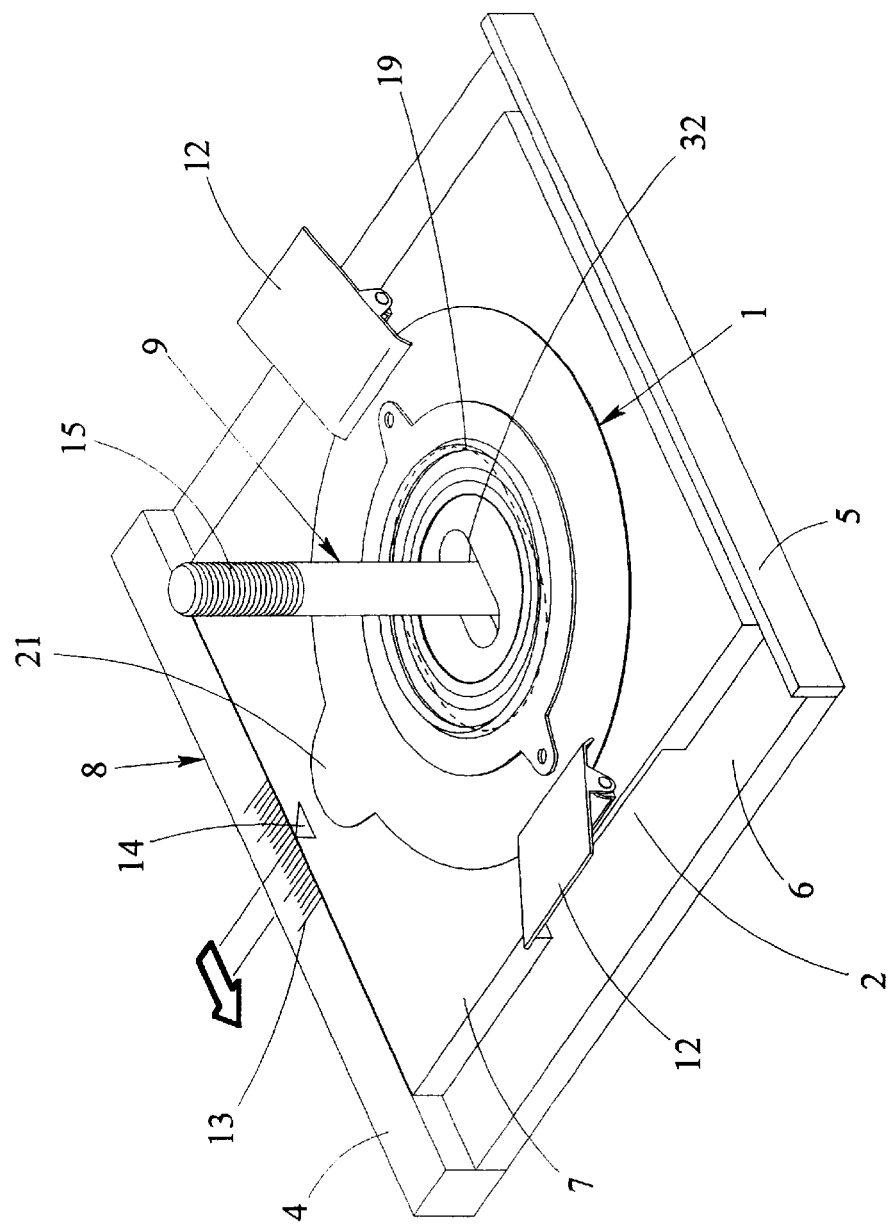
FIG. 3 is a perspective view, which corresponds to FIG. 1, showing the condition in which a cutter and a knob are removed after the completion of a stoma wafer boring operation.

A stoma wafer boring operation. is carried out in the following order. First, with reference to the parts seen in a vertically spaced state in FIG. 2, the stoma wafer 1 is fitted around the guide rod 9 with the reference mark 14 aligned with the center of the scale 13, the stoma wafer 1 being positioned and fixed on the upper base member 7 by the clips 12, 12. After the cutter 10 is fitted around the guide rod 9, the knob 11 is moved down as it is screwed on the guide rod 9 in the condition shown in FIG. 1. When the circular edge 16 is sharp with the cutter 10 sufficiently heavy, the stoma wafer 1 can be cut circularly by only fitting the cutter. 10 around the guide rod 9 but, in order to carry out the cutting operation reliably, it is necessary that the cutter 10 be pressed down by the knob 11. When the circular edge 16 bites the receiving surface 19 of an ABS resin with a resistance preventing a further downward movement of the cutter 10 detected, the screwing of the knob 11 on the guide rod 9 is stopped. The condition of the stoma wafer 1 which has thus finished being subjected to an initial boring operation is seen in FIG. 3.

Since, in this example, a laterally elongated, substantially elliptic hole 20 (refer to FIGS. 5 and 6) is made in the stoma wafer 1 (a projecting portion 21 indicates the upper side, refer to FIG. 3), the upper base member 7 is moved as the reference mark 14 with respect to the scale 13 is observed. Since the cutter 10 moves down along the guide rod 9, the stoma wafer 1 is slid in the direction opposite to the direction in which the desired substantially elliptic hole 20 extends. In order to extend the substantially elliptic hole 20 in the direction other than the direction in which the upper base member 7 is slid, the clips 12, 12 are once removed, and the stoma wafer 1 is reset so as to change the direction in which it faces. In FIG. 3, both the cutter 10 and knob 11 are removed from the guide rod 9 for the convenience of. description the operation. When the circular edge 16 is not in contact with the stoma wafer 1, the stoma wafer 1 can be moved as it is with the upper base member 7.

Figure 4:
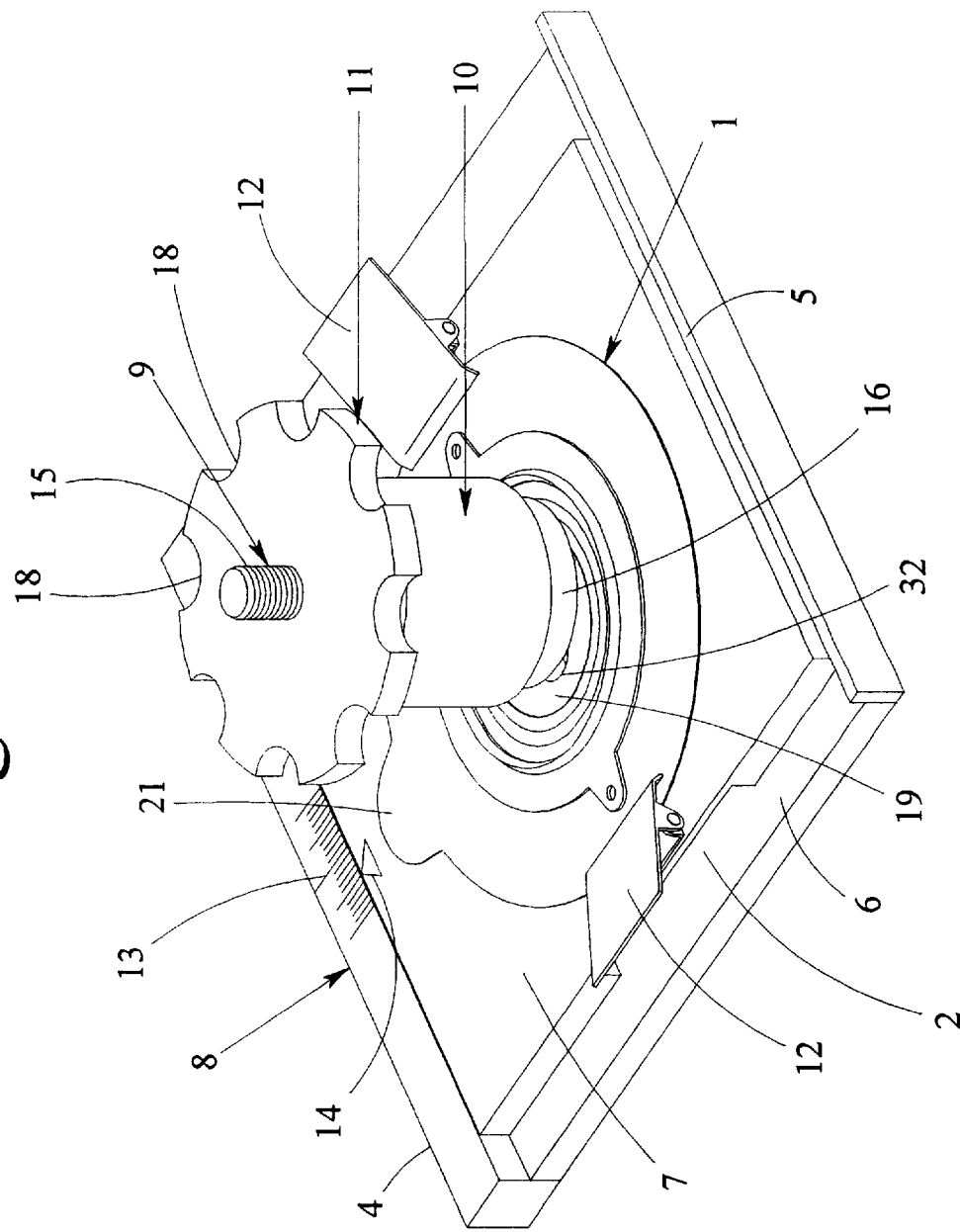
FIG. 4 is a perspective view, which corresponds to FIG. 1, showing the condition of a second boring operation being carried out.
Figure 5:
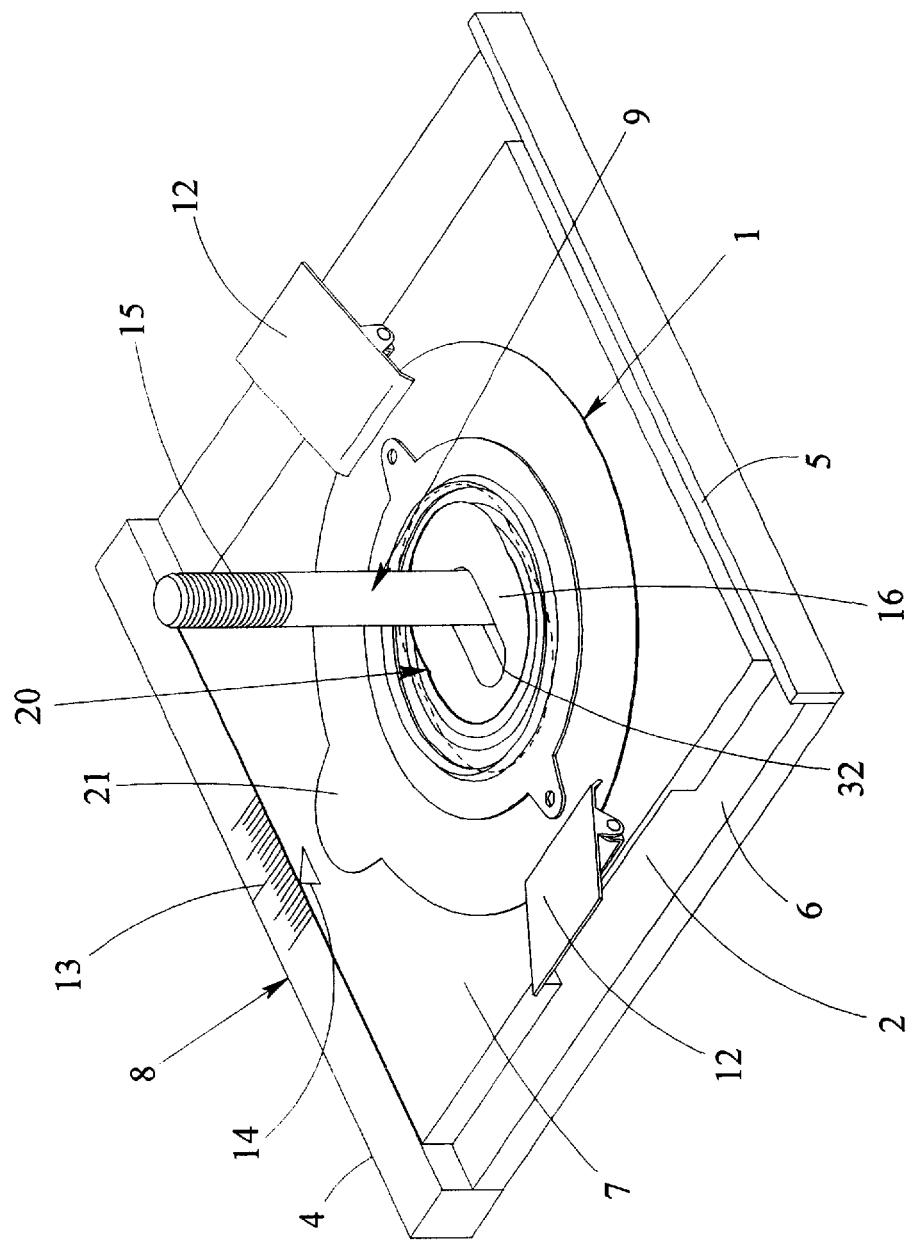
FIG. 5 is a perspective view, which corresponds to FIG. 1, showing the condition in which the cutter and knob are removed after the completion of the second boring operation.
Figure 6:
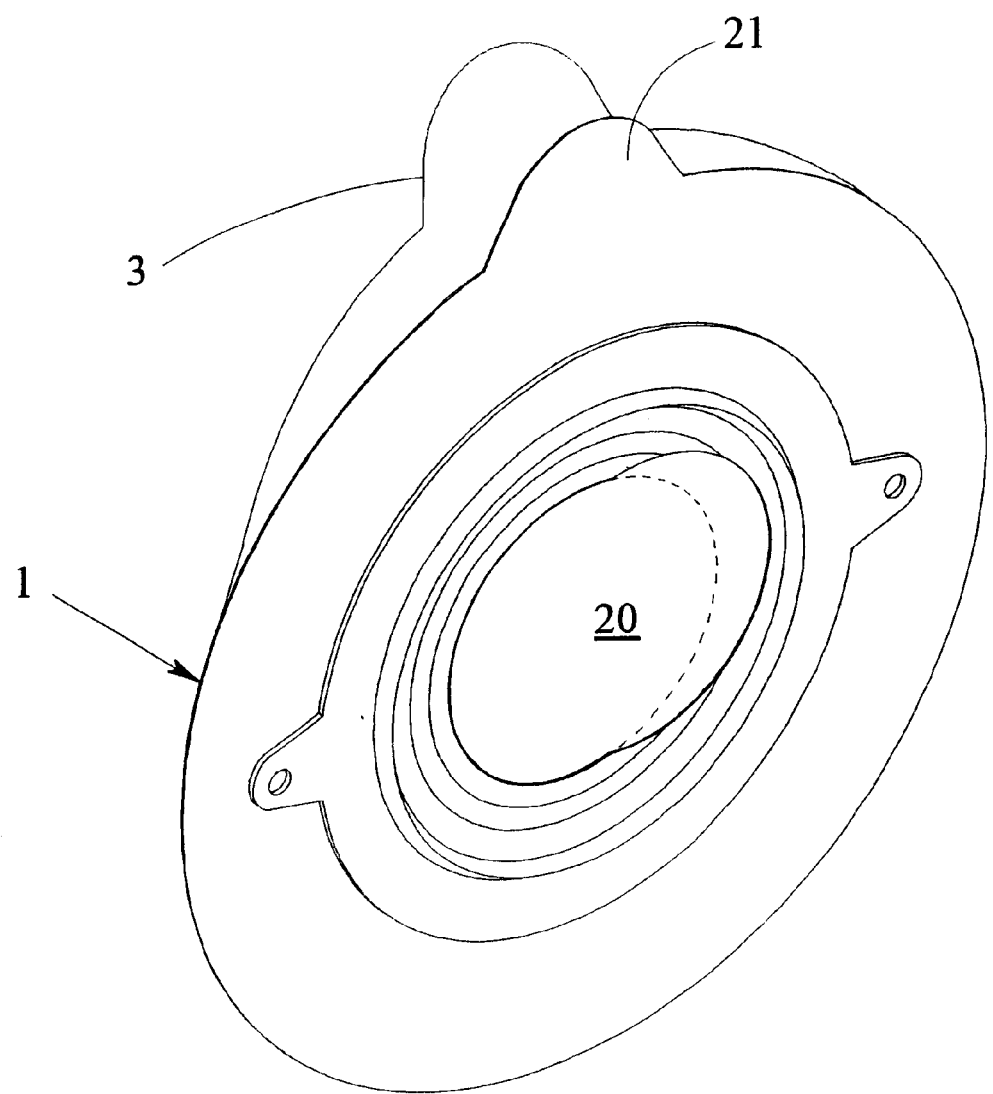
FIG. 6 is a perspective view showing the condition in which a peelable film is being removed from a stoma wafer which has finished being bored.

Thus, a second boring operation is executed for the, stoma wafer 1 which has been slid by a required. amount as seen in FIG. 4. As is clear from FIG. 4, the circular edge 16 is moved down on the portion of-the stoma wafer 1 slid with the upper base member 7 which deviates rightward from the center of the hole previously made, and, in this condition, a substantially elliptic hole 20 can be formed as seen in FIG. 5. After the boring operation is finished, the stoma wafer 1 is removed from the guide rod 9, and used by removing the peelable film 3 therefrom as seen in FIG. 6. In this example, the amount by which the upper base member 7 is slid is shown to be large for the convenience's sake but a larger diameter of a practically required substantially elliptic hole 20 is longer than a smaller diameter thereof by only around 1–2 mm. The scale 13 is indispensable for accurately grasping such a fine shift of the upper base member 7.

Figure 7:
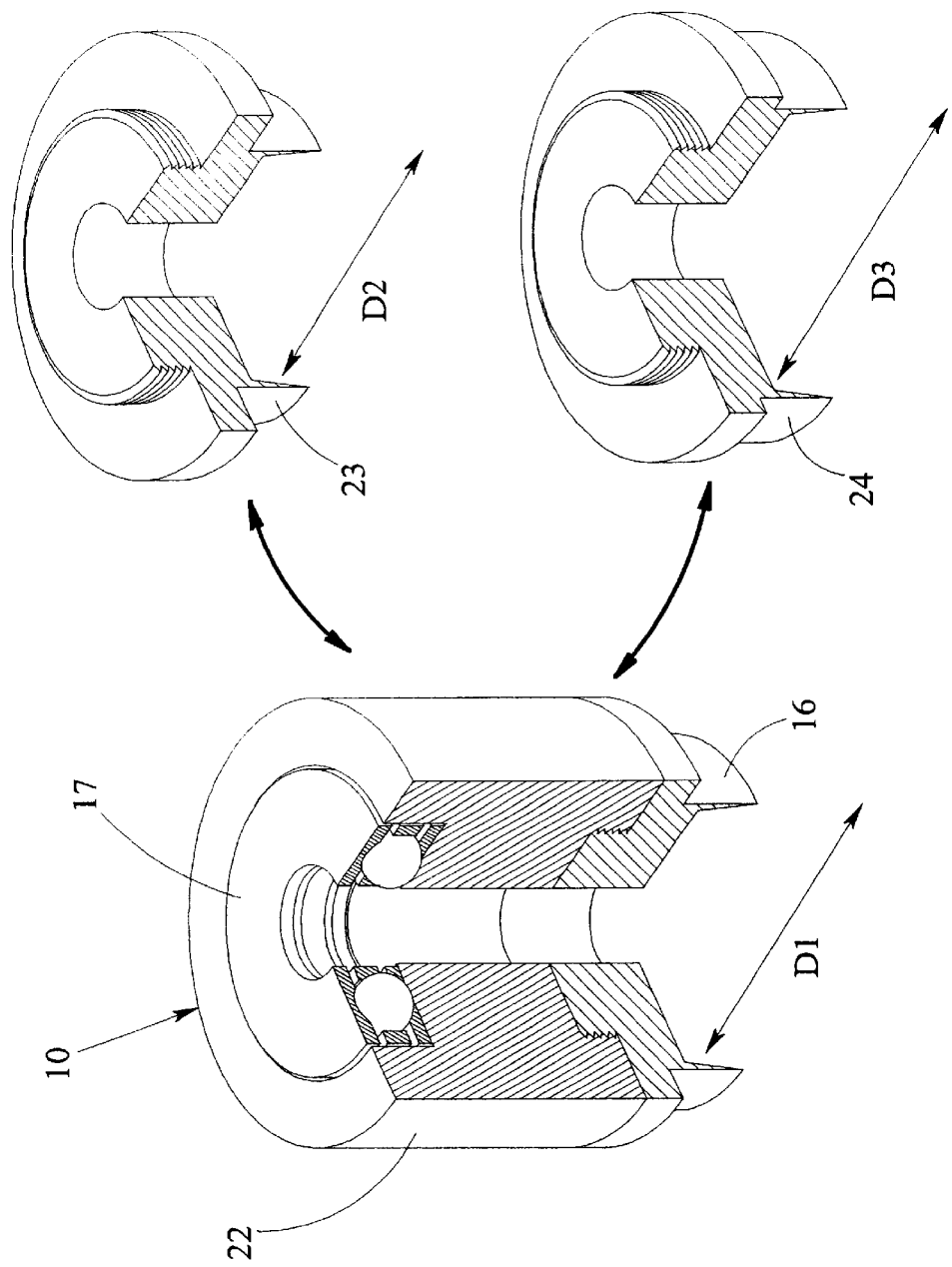
FIG. 7 is a perspective view of a cutter a circular edge only of which is replaceable.

In this example, the circular edge 16 is integral with a body of the cutter 10, so that, when a substantially elliptic hole of a different diameter is required, the cutter 10 has to be replaced. In view of the matter, it is convenient to prepare a cutter 10 divided into a circular edge 16 and a cutter body 22 as seen in FIG. 7, and suitably attach in place of the circular edge 16 one of circular edges 23, 24 of diameters D2, D3 different from the diameter D1 of the circular edge 16 to the cutter body 22. Such a mode of replacing the circular edge has advantages that only a circular edge replacing operation serves the purpose without requiring the replacement of the cutter as a whole when the circular edge is broken.

Figure 8:
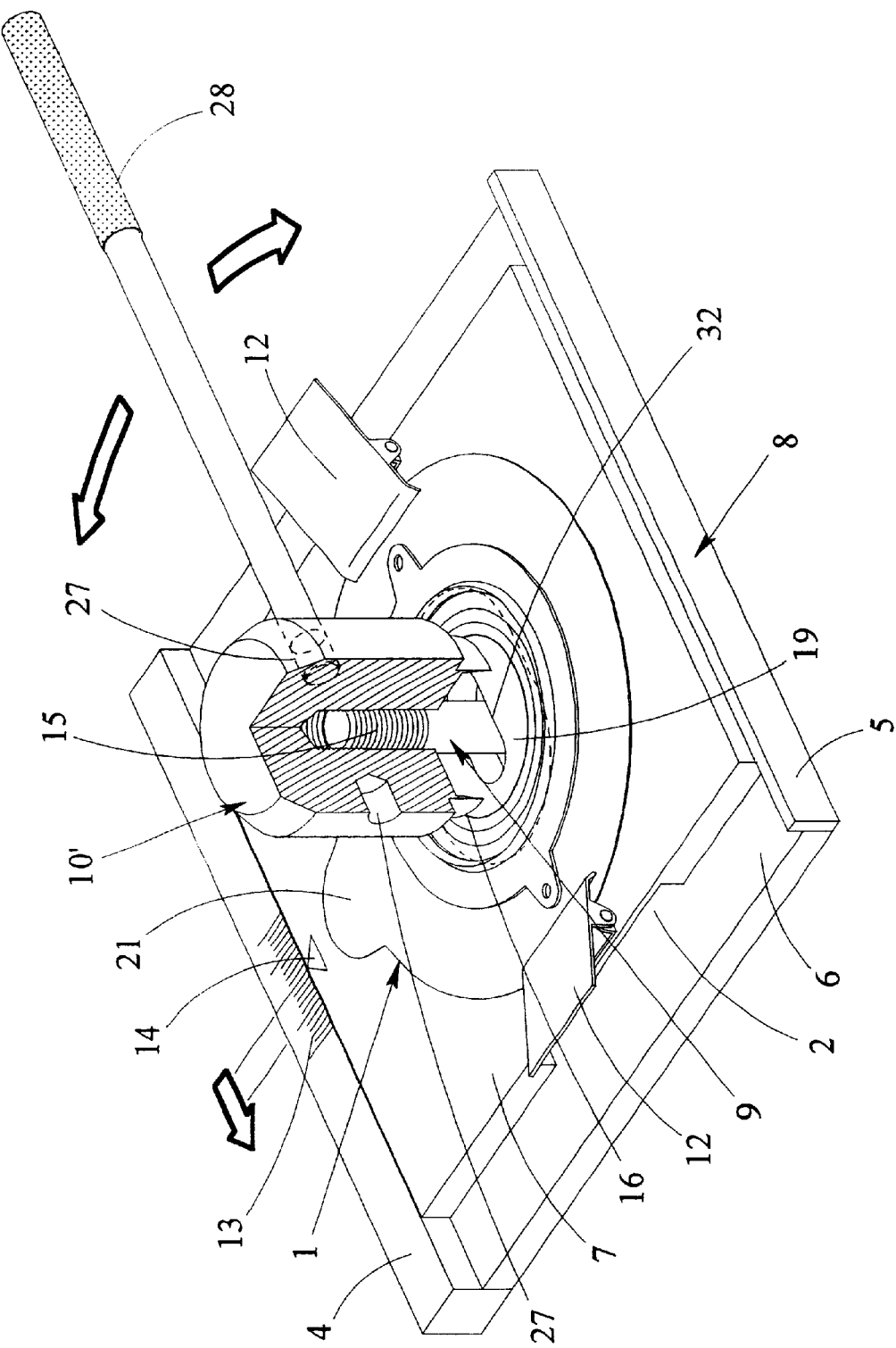
FIG. 8 is a perspective view, which corresponds to FIG. 1, of an apparatus for boring stoma wafers, formed by screwing a cutter directly on a guide rod.

The apparatus for boring stoma wafers seen in FIG. 8 has a structure in which a cutter 10' having a circular edge 16 is screwed on a guide rod 9. In this example, the circular edge 16 cuts a stoma wafer 1 as the former is turned in accordance with the screwing of the cutter 10' on the guide rod 9, to make a hole in the latter. In order to form an elliptic hole in the stoma wafer 1 the upper base member 7 is slid with the stoma wafer 1 after an initial operation for making a hole therein is finished, and a boring operation is carried out again. The upper base member 7 is provided thereon with reference mark 14, while the lower base member 6 is provided on its side edge guide 4 with scale 13 opposed to the reference mark 14. Although the cutter 10' may be directly twisted, an auxiliary handle 28 inserted into an insert hole 27 provided in a side surface of the cutter 10' is turned in this example, to reduce labor.

Figure 9:
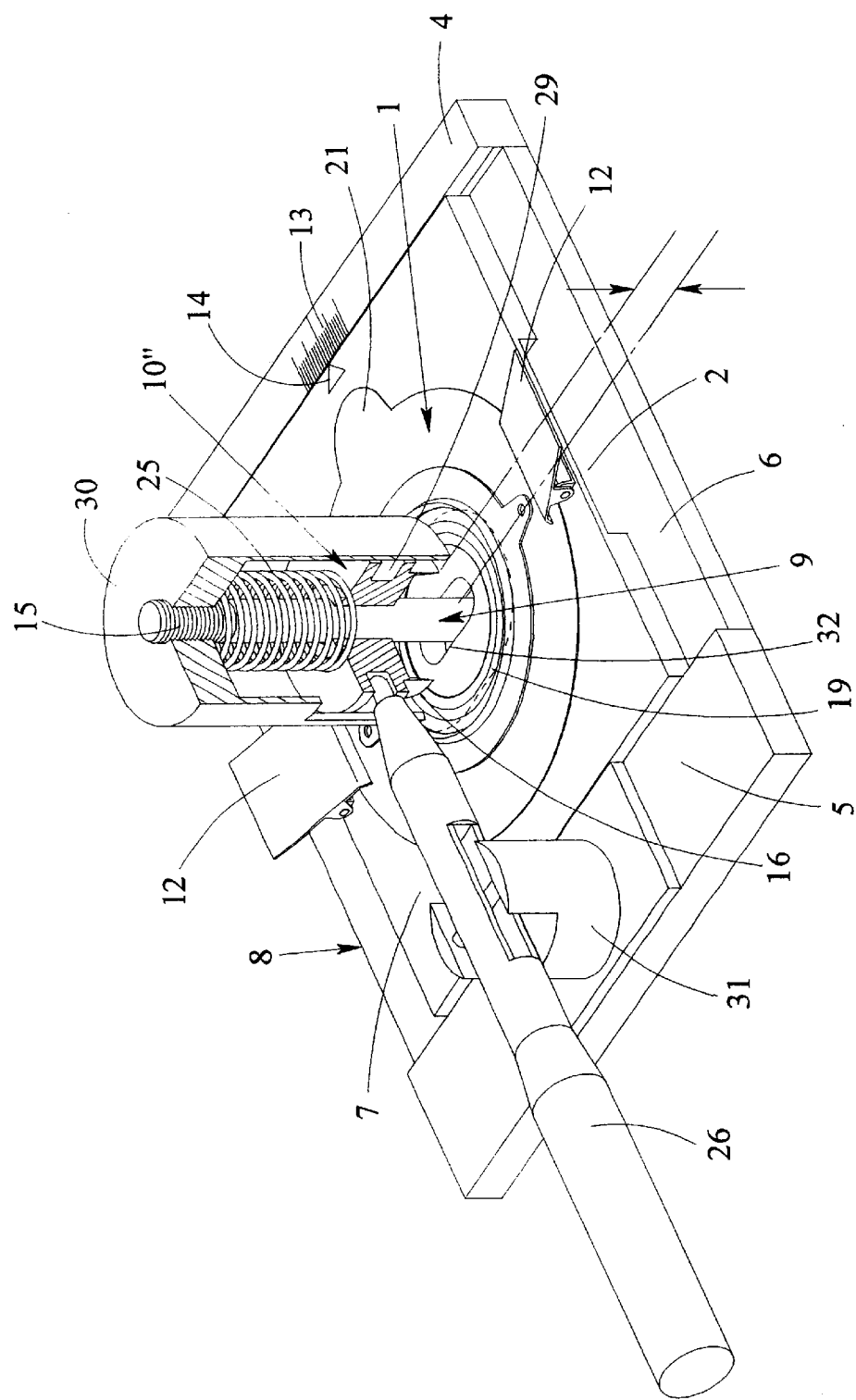
FIG. 9 is a perspective view, which corresponds to FIG. 1, showing the condition in which a cutter is lifted by a support handle in a stoma wafer boring apparatus of the type in which the cutter is brought down onto a stoma wafer.

In these two examples, the circular edge 16 is pressed against the stoma wafer 1 by the screwing operation of the cutter 10' but the level of the circular edge pressing force differs depending upon the workers. When the circular edge 16 is therefore stricken against the stoma wafer 1 by utilizing a spring 25 as seen in, for example, FIG. 9, the level of the pressing force of the circular edge 16 against the stoma wafer 1 becomes substantially constant, and an inner circumferential edge of a hole 20 thus cut becomes sharp. In the example of FIG. 9, a cutter 10" provided with a circumferential groove 29 in a side surface thereof is fitted around a guide rod 9, and the spring 25 is interposed between a cover 30, which is screwed on the guide rod 9 for fixing the position of the cutter 10, and the cutter 10".

Figure 10:
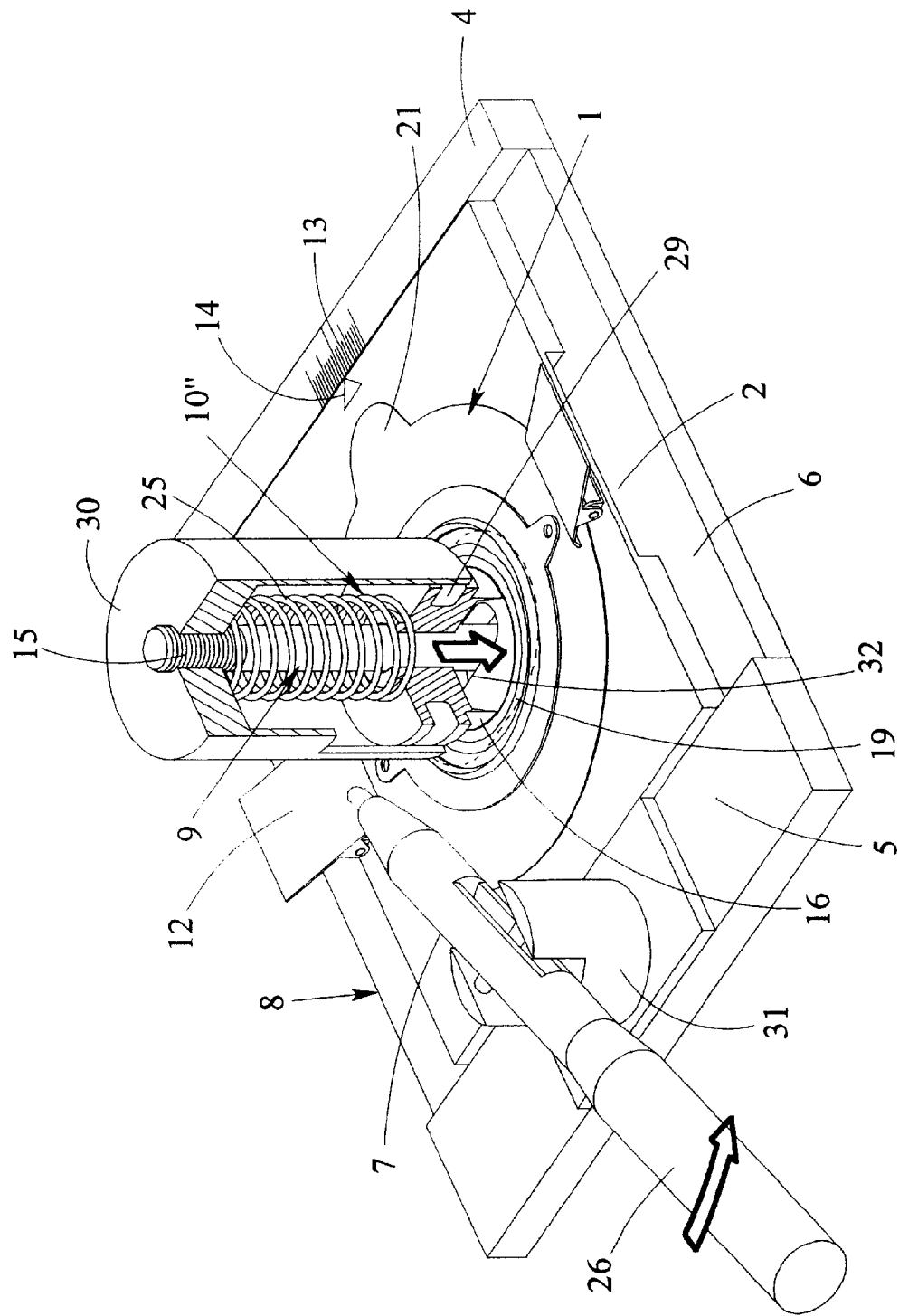
FIG. 10 is a perspective view, which corresponds to FIG. 1, of the same apparatus for boring stoma wafers in the condition in which the support handle is released to bring down the cutter onto the stoma wafer.

When a support handle 26 joined via a shaft to a support base 31 provided on a side edge guide 5 of a lower base member 6 is inserted at a free end portion thereof into the circumferential groove 29 to lift the cutter 10", the cutter 10" is moved up as it compresses the spring 25. When the support handle 26 is then released either leftward or rightward as seen in FIG. 10, the cutter 10" is brought down owing to the expansion of the spring 25, so that the circular edge 16 momentarily cut the stoma wafer 1 to finish the boring operation. After the initial boring operation is finished, the worker slides the upper base member 7 with the stoma wafer 1, and carries out a second boring operation to form a substantially elliptic hole 20.

FIGS. 11–14 shows examples of the apparatus for boring stoma wafers in which a guide rod is not set on a base 8. None of these examples has a projection on a receiving surface 19 except a slightly protruding stoma wafer positioning projection 44, so that the withdrawing and placing of a stoma wafer from and on the receiving surface 19 are done easily.

In the apparatus for boring stoma wafers in which the cutter 100 is urged upward, a Same 36 of a bridge structure is provided between side edge guides 4, 5 of a lower base member 6, and a lever 35 is joined via a shaft to the fame 36, a rod-carrying cam 34 being joined via a shaft to the portion of the lever 35 which is in the vicinity of an end portion thereof, and which can be pressed from the upper side. The rod-carrying cam 34 comprises a disc 39 to which an operating rod 38 is fixed. The disc 39 has an eccentric pivot 40. Therefore, when the rod 38 is tuned in the raising direction thereof (FIG. 12), a circumferential portion of the disc 39 gradually presses down the lever 35. The cutter 100 has the circular edge 16 on the lower s thereof, and the guide rod 9 set up on an upper surface thereof, the guide rod 9 being passed through the frame 36 and engaged with a lower surface of the lever 35. The cutter 100 is lifted toward the frame 36 by the coiled spring 33 fitted around the guide rod 9, and it is constantly urged upward. Accordingly, the circular edge 16 is normally away from the base 8 to cause the lever 35 to be raised.

When the rod 38 of the rod-carrying cam 34 is turned up (FIG. 12), the portion of a circumferential surface of the disc 39 which is long distance away from the eccentric pivot 40 presses down the lever 35. Consequently, the guide rod 9 engaged with the lever 35 and the cutter 100 are pressed down to enable the stoma wafer (not shown) placed on the base 8 to be bored. The guide rod can also be pressed down directly not via the lever by a circumferential surface of the rod-carrying cam 34. When a structure for turning down the lever 35 by the rod-carrying cam 34 is employed as in this example, the force applied to the rod 38 can be amplified owing to a moment ratio (a portion to be gripped of the rod 38~ the eccentric pivot 40 of the disc 39: a pressing portion of the lever 35 the eccentric pivot 40 of the disc 39, a portion to be pressed of the lever 35~ a pivot 41 of the lever 35: a pressing portion of the guide rod 9~ the pivot 41 of the lever 35). Moreover, since a ratio of an amount of a vertical movement of the cutter 100 to that of a turning movement of the rod 38 decreases, the vertical movements of the cutter 100 can be made more finely.

Figure 11:
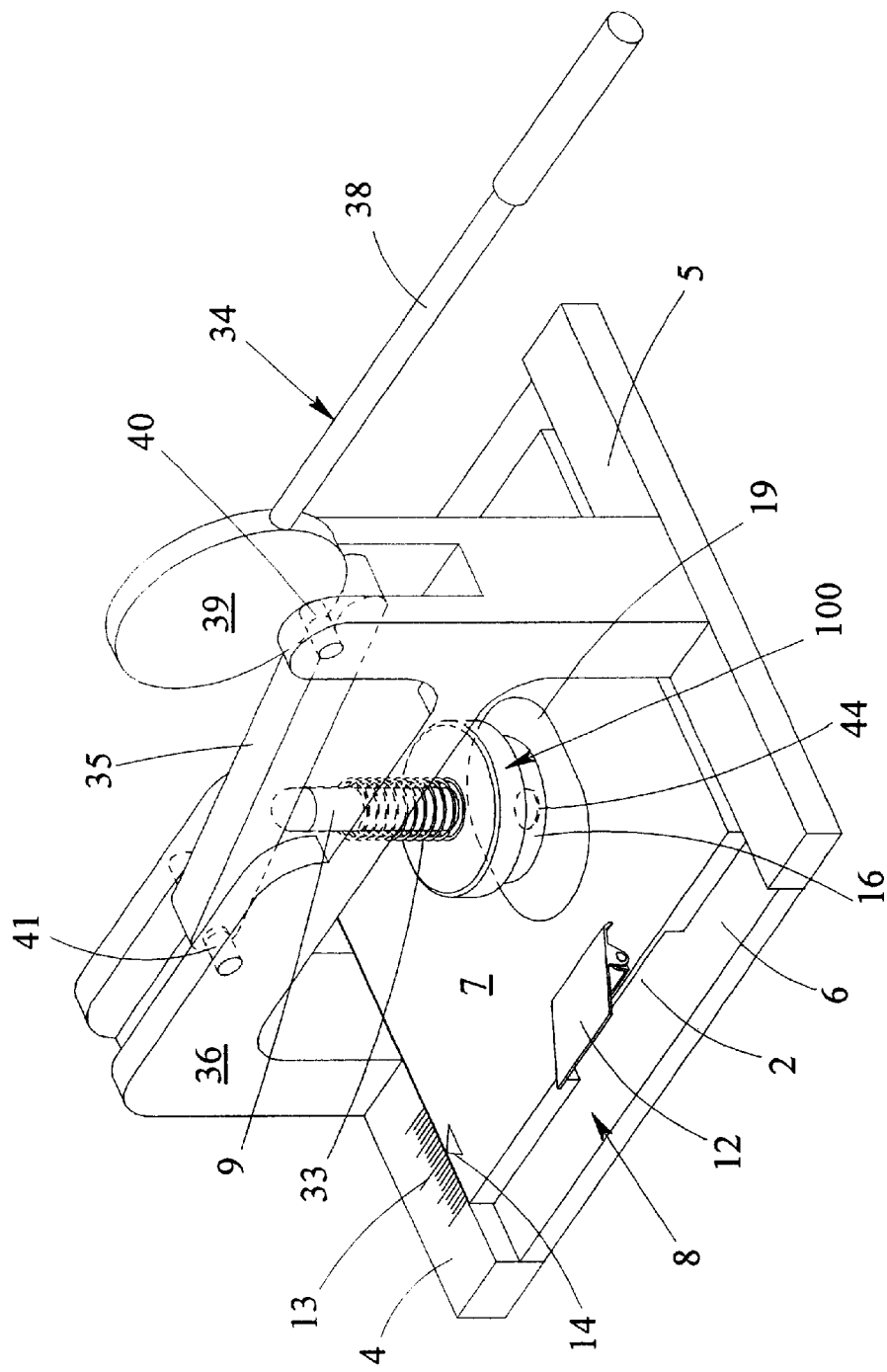
FIG. 11 is a perspective view of an apparatus for boring stoma wafers of the type in which a cutter is urged upward by a coiled spring fitted around a guide rod, showing a rod-carrying cam not yet turned.
Figure 12:
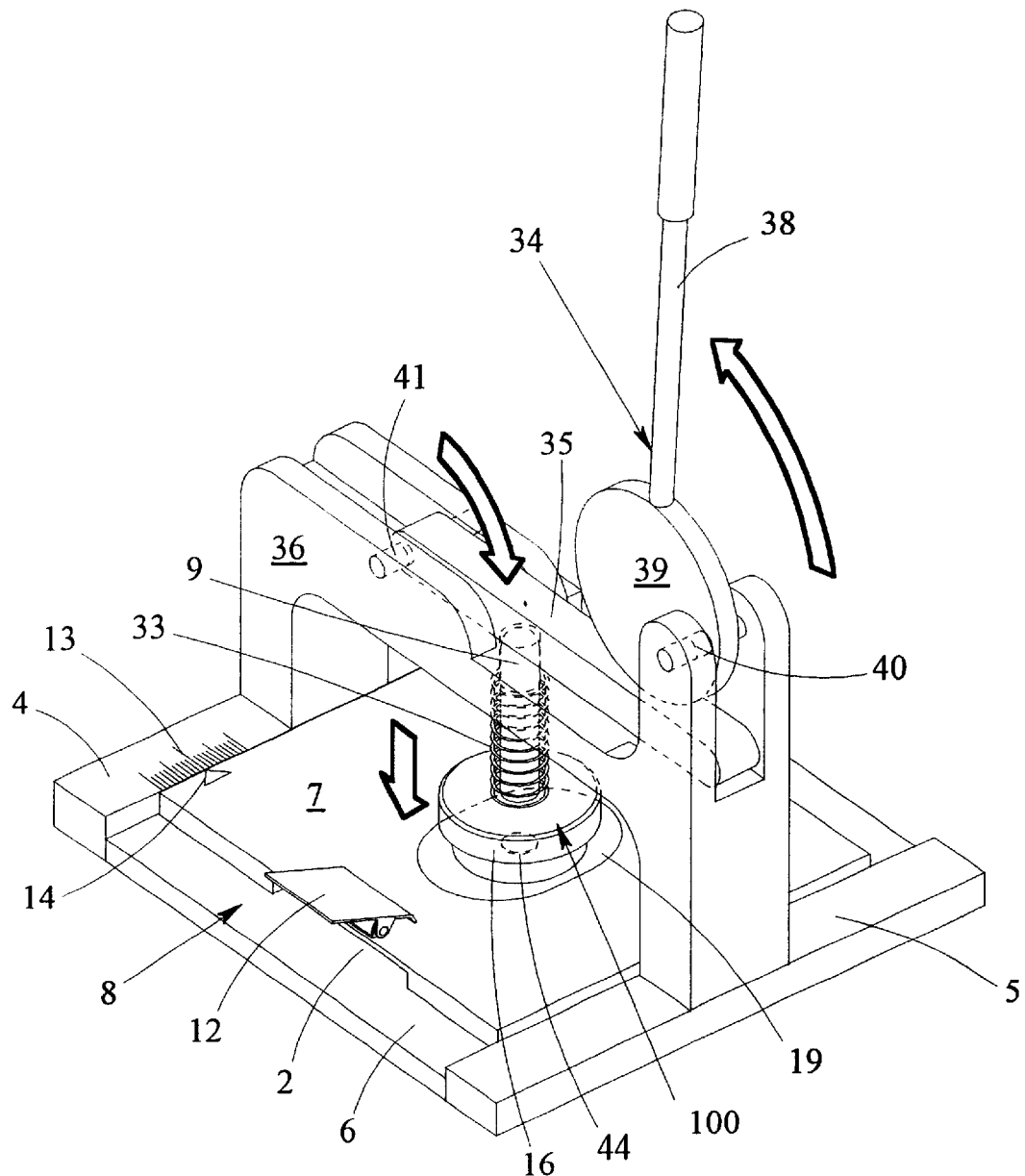
FIG. 12 is a perspective view of the same apparatus for boring stoma wafers in which the rod-carrying cam has just been turned.
Figure 13:
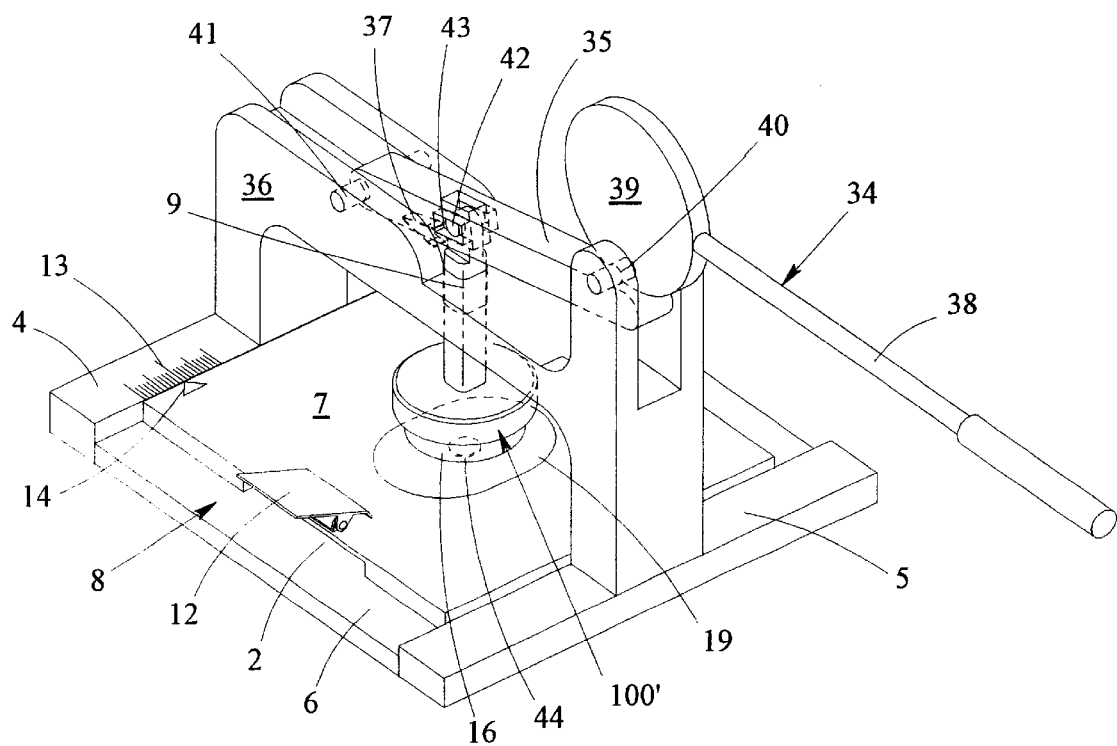
FIG. 13 is a perspective view of an apparatus for boring stoma wafers of the type in which a lever is urged in the standing direction thereof, showing a rod-carrying cam not yet turned.
Figure 14:
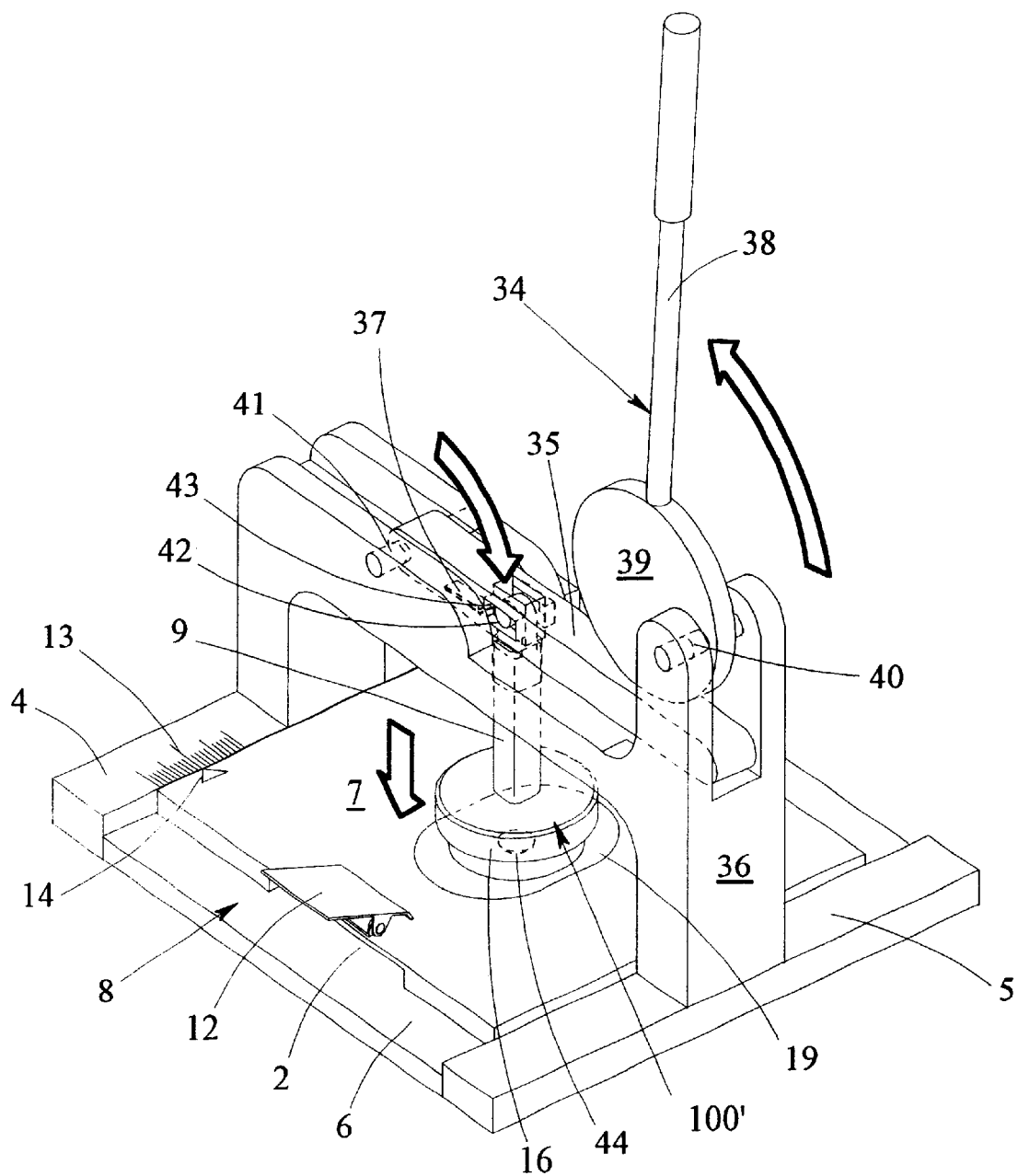
FIG. 14 is perspective view of the same apparatus for boring. stoma wafers in which the rod-carrying cam has just been turned.

The apparatus for boring stoma wafers seen in FIGS. 13 and 14 is basically identical with the example of FIGS. 11 and 12. The differences between these examples reside in that the example of FIGS. 13 and 14 is provided with a locking portion 42 at an upper end of a guide rod 9 set up on a cutter 100', the locking portion 42 being fitted in a slide groove 43 formed in a lever 35, to operatively connect the cutter 100' and lever 35 together. To effect the operative connection of these parts, a plate spring 37 which urges the lever 35 in the standing direction thereof is provided between a Same 36 and lever 35. This example is advantageous in that the guide rod 9 is completely joined to the lever 35 to enable a turning movement of the lever 35 and a vertical movement of the cutter 100' to be made in accordance with each other reliably.

According to the present invention, a non-circular (substantially elliptic) hole having a beautiful inner circumference can be provided easily in a stoma wafer even by a user's boring operation. Above all, a fine cutting operation for obtaining a substantially elliptic hole can be carried out far more accurately and easily as compared with that in a conventional apparatus of this kind. Even a mere regular use of a stoma wafer makes a user feel troublesomeness and inconvenience. The present invention is preferable as a means for eliminating such nuisance and inconvenience even to a small extent.

What is claimed: is:

1. An apparatus for boring stoma wafers, said apparatus comprising:
    a base on which a stoma wafer is placed, said base comprising an upper base member on which said stoma wafer is placed and a lower base member with said upper base member movably supported on said lower base member so that said upper base member can be moved freely;
    a guide rod provided on said lower base member and extending through an elongated hole in said upper base member; and
    a circular cutter for making a circular hole in said stoma wafer placed on said upper base member and provided on said guide rod; and
    wherein said guide rod restricts vertical and lateral movement of said cutter whereby a non-circular hole comprising at least two staggered circular holes can be accurately bored in said stoma wafer by said circular cutter by moving said upper base member on said lower base member between at least two different positions.

2. An apparatus for boring stoma wafers according to claim 1, wherein said upper base member is provided with said elongated hole extending in the moving direction thereof, said guide rod which can be inserted into a hole made in the stoma wafer being set up on said lower base member through said elongated hole, and said cutter being fitted around said guide rod and pressed down by a knob which is moved down as said knob is screwed on said guide rod.

3. An apparatus for boring stoma wafers according to claim 1, wherein said upper base member is provided with said elongated hole extending in the moving direction thereof, said guide rod which can be inserted into the a hole made in the stoma wafer being set up on said lower base member through said elongated hole, and said cutter itself being moved down as said cutter is screwed on said guide rod.

* * * * *